United States Patent [19]

Itsuji et al.

[11] Patent Number: 4,944,274

[45] Date of Patent: Jul. 31, 1990

[54] AIR-FUEL RATIO CONTROL APPARATUS FOR INTERNAL COMBUSTION ENGINES

[75] Inventors: Takayuki Itsuji, Novi, Mich.; Sadayasu Ueno, Katsuta; Norio Ichikawa, Mito, both of Japan

[73] Assignees: Hitachi, Ltd, Tokyo; Hitachi Automotive Engineering Co., Ibaraki, both of Japan

[21] Appl. No.: 417,075

[22] Filed: Oct. 4, 1989

[30] Foreign Application Priority Data

Oct. 11, 1988 [JP] Japan ................. 63-253774

[51] Int. Cl.$^5$ .......................... F02M 51/00
[52] U.S. Cl. .......................... 123/489; 123/440
[58] Field of Search ................. 123/489, 440

[56] References Cited

U.S. PATENT DOCUMENTS 4,834,051 5/1989 Tanaka et al. ............... 123/489
4,842,711 1/1989 Asakura et al. .............. 123/489
4,860,712 8/1989 Nakajima et al. ............. 123/489

FOREIGN PATENT DOCUMENTS

0096753 5/1987 Japan ....................... 123/489
0073148 3/1989 Japan ....................... 123/489
2195772 4/1988 United Kingdom ............. 123/489

Primary Examiner—Raymond A. Nelli
Attorney, Agent, or Firm—Antonelli, Terry, Stout & Kraus

[57] ABSTRACT

An air-fuel ratio control apparatus for an internal combustion engine includes a solid electrolyte having a first electrode disposed on one surface thereof to contact with the atmosphere and a second electrode disposed on the other surface thereof to contact with the exhaust gas from the engine through a diffusing resistor, and means for applying a voltage across the first and second electrodes to detect an oxygen pump current flowing in the solid electrolyte whereby a correction factor relating to a change in the diffusion coefficient of the diffusing resistor is computed so that the oxygen pump current detected by the detecting means is corrected in accordance with the correction factor and the air-fuel ratio of the exhaust gas is determined in accordance with the corrected oxygen pump current, thereby controlling the quantity of fuel supplied to the engine in accordance with the determined air-fuel ratio.

8 Claims, 8 Drawing Sheets

EXHAUST GAS | ATMOSPHERE

AIR-FUEL RATIO CONTROL APPARATUS FOR INTERNAL COMBUSTION ENGINES

BACKGROUND OF THE INVENTION

The present invention relates to an air-fuel ratio control apparatus for internal combustion engines and more particularly to such air-fuel ratio control apparatus including means for calibrating the output characteristic of an air-fuel ratio sensor against its change with time due to any dirt or pollution of the air-fuel ratio sensor.

In a known apparatus of this type such as disclosed in JP-A-58-57050, there is provided a discriminating unit which utilizes the atmosphere as a known air-fuel ratio for the calibration of a variation with time of the output characteristic of an air-fuel ratio so as to determine whether the surrounding of the sensor is filled with the air whereby in response to the discriminating unit, a correction factor for the air-fuel ratio sensor output characteristic is calculated and the desired calibration is effected when the surrounding of the air-fuel ratio sensor is filled with the air.

In the above-mentioned conventional technique, since there is practically no chance of the sensor surrounding being filled with the air, a situation is caused where the output characteristic of the sensor is not calibrated in a long period of time. There is a problem especially in the case of an automobile equipped with an automatic transmission or in the case of an automobile driven by the driver without using engine braking.

SUMMARY OF THE INVENTION

It is an object of the present invention to provide an air-fuel ratio control apparatus so designed that the output characteristic of an air-fuel ratio sensor is certainly calibrated thereby accurately controlling the mixture into the engine.

To accomplish the above object, in accordance with the present invention there is thus provided an air-fuel ratio control apparatus for internal combustion engines in which the oxygen pump current flowing in an air-fuel ratio sensor is stopped whereby the restoration time of the electromotive force is measured to calibrate the output characteristic of the air-fuel ratio sensor on the basis of the measured result.

The air-fuel ratio sensor is controlled by an oxygen pump current in such a manner that the electromotive force between its measuring electrode and reference electrode or the potential difference between the electrodes attains a given value. This is equivalent to controlling in such a manner that the oxygen partial pressure in the diffusing resistor layer and the oxygen partial pressure on the reference electrode side respectively attain given values. By thus stopping the oxygen pump current, the electromotive force is changed from its controlled value to a value corresponding to the air-fuel ratio of the exhaust gas, that is, it is changed to substantially 0 V if the air-fuel ratio is lean and to substantially 1 V if rich. Thus, the various gases in the exhaust diffuse naturally into the diffusing resistor layer and the air-fuel ratio in the diffusing resistor layer becomes equal to that of the exhaust gas, with the result that the oxygen partial pressure in the diffusing resistor layer is close to the oxygen partial pressure of the atmosphere when the air-fuel ratio is lean but very small when rich and produced between the electrodes is an electromotive force which is proportional to the difference between the oxygen partial pressures near between the electrodes. As a result, after the oxygen pump current has been stopped, the electromotive force is restored to a value corresponding to the air-fuel ratio in the diffusing resistor layer. By virtue of this change in the restoration time of the electromotive force, it is possible to know the rate of change of the diffusion constant of the diffusing resistor layer. Also, it is known that the amount of oxygen pump current for the same air-fuel ratio is determined by the diffusion constant if the areas of the electrodes and the sensor temperature are the same. Therefore, if the rate of change of the diffusion constant is known, the output characteristic of the air-fuel sensor can be calibrated thereby performing the air-fuel ratio control accurately.

DESCRIPTION OF THE PREFERRED EMBODIMENTS

An embodiment of the present invention will now be described with reference to the drawings.

Figure 2:
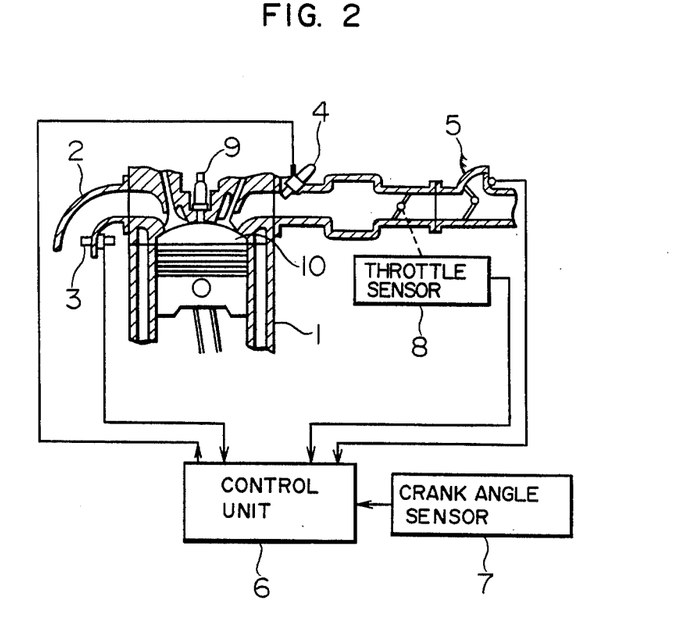
FIG. 2 is an engine control system diagram.

In FIG. 2, in accordance with the signals from an air flow meter 5 attached to the intake side of an internal combustion engine 1, a throttle sensor 8 for indicating the opening of the throttle valve and a crank angle sensor 7 for detecting the rotational speed and rotational angle of the engine 1, a control unit 6 computes a fuel injection time, fuel supply time or intake air quantity so that in accordance with the computed value fuel is supplied by a fuel injector 4 or any other actuator and the fuel is mixed with the intake air thus forming a mixture. The mixture is introduced into a cylinder 10 and the mixture is ignited and exploded by a spark plug 9. The exhaust gases resulting from the explosion are discharged through an exhaust manifold 2. The air-fuel ratio of the exhaust gases is detected by an air-fuel ratio sensor 3 attached to the exhaust manifold 3 so that in accordance with the detection signal the control unit 6 computes the deviation from the desired air-fuel ratio and the fuel injection time, the fuel supply time or the like is corrected.

Figure 3:
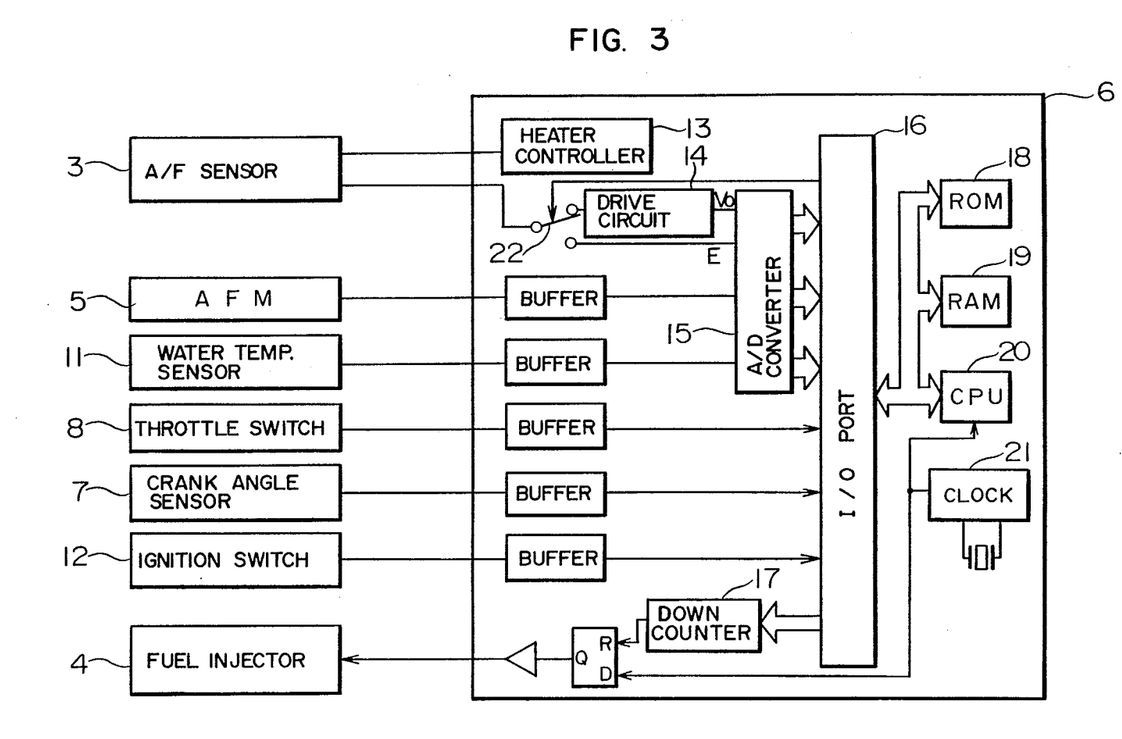
FIG. 3 is a block diagram of the control unit.

FIG. 3 is a detailed block diagram of the control unit 6. The signal from the air flow meter 5 is converted to a digital signal by an A/D converter 15 and then sent to an I/0 port 16. The signal from the crank angle sensor 7 is directly sent to the I/0 port 16 where the number of pulses is counted to detect the rotational speed of the engine 1. On the basis of these two signals, a CPU 20 computes a basic injection time in accordance with the program stored in an ROM 18 by a well known method.

Also, a sensor drive circuit 14 is connected through a switch 22 to the air-fuel ratio sensor 3 for detecting the condition of the exhaust gases so that the detection signal $V_0$ from the sensor 3 is applied to the A/D converter 15 which in turn converts the signal to a digital signal. This digital signal is then read into the CPU 20 through the I/0 port 16. As will be described later, in accordance with this value and the signals from the other sensors 7, 8, 11 and 12, a correction factor for the basic injection time is computed and the proper injection time is determined thereby controlling the engine 1 to the proper air-fuel ratio.

Figure 4:
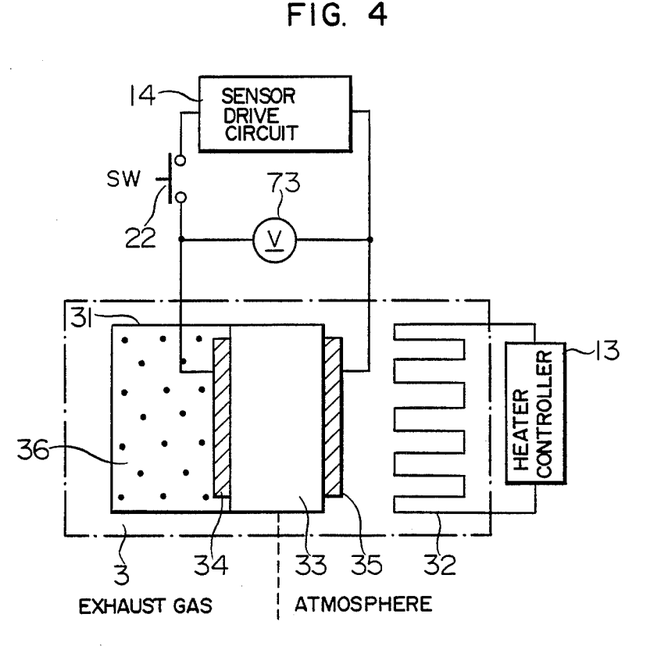
FIG. 4 is a diagram showing the principle of the air-fuel ratio sensor.
Figure 5:
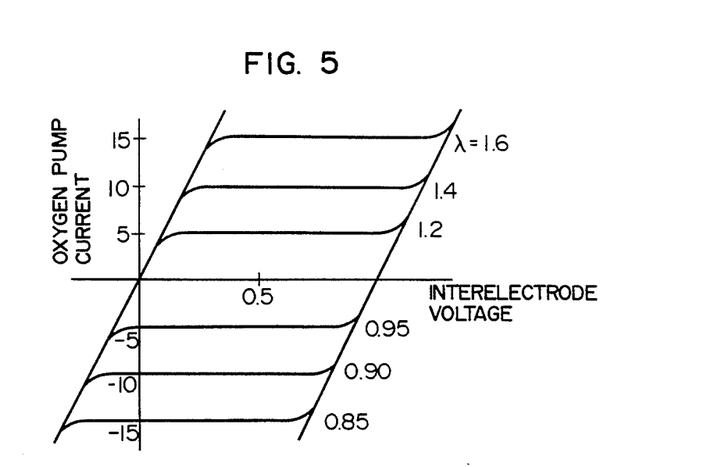
FIG. 5 is a characteristic diagram showing the relation between the voltage applied to the air-fuel ratio sensor and the oxygen pump current.
Figure 6:
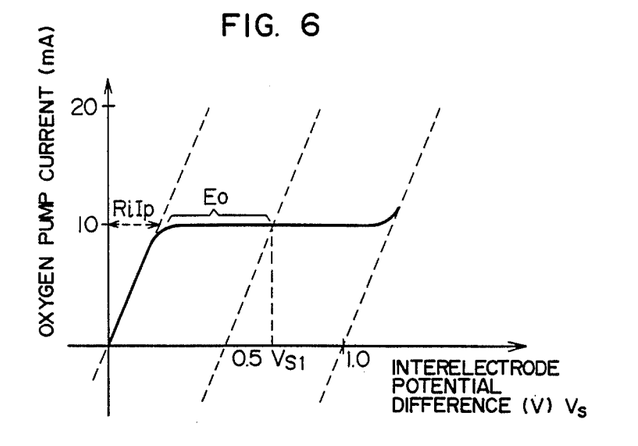
FIG. 6 is a detailed diagram of the applied voltage-oxygen pump current characteristic.

The construction and operation of the air-fuel ratio sensor 3 will now be described with reference to FIGS. 4 and 5. The air-fuel ratio sensor 3 includes a sensor cell 31 and a heater 32, and the cell 31 includes an oxygen ion conductor-type solid electrolyte 33, electrodes 34 and 35 having catalytic performance which are respectively arranged on the sides of the solid electrolyte 33 and a porous or single-perforated diffusing resistor layer 36 arranged on the electrode 34 so as to be exposed to the exhaust gas. The other electrode 35 is exposed to atmosphere serving as a reference gas, and the two gases are shielded from each other to prevent them from mixing together. The heater 32 and a heater controller 13 control the sensor cell 31 to attain a given preset temperature within its operable temperature range of 600° C. to 900° C. With the air-fuel ratio sensor 3 maintained at the given temperature, if a voltage (of a positive polarity toward the electrode 35) is applied across the electrodes 34 and 35 in a direction such that oxygen is pumped out toward the atmosphere from the diffusing resistor layer side through the solid electrolyte, a current flows as shown in FIG. 5. This is referred to as an oxygen pump current and its flat portion changes between the high and low levels depending on the air-fuel ratio of the exhaust gas. Thus, by detecting the flat portion of the oxygen pump current, it is possible to detect the air-fuel ratio. The oxygen pump current will be explained in greater detail with reference to FIG. 6. Since the sensor cell has an internal resistance $R_i$, the flow of an oxygen pump current $I_p$ a voltage drop of $R_i I_p$ in the region where the interelectrode potential difference $V_s$ is small. When the interelectrode potential difference $V_s$ becomes greater than a certain value, the oxygen pump current saturates thus showing a flat characteristic. The reason is that the diffusion of oxygen to the surface of the electrode 34 through the diffusing resistor layer 36 is subjected to rate determination by the diffusing resistor layer 36 so that the oxygen pump current $I_p$ is maintained constant even if the voltage is increased. However, where the air-fuel ratio is on the rich side, the diffusion of unburned gases in the exhaust is subjected to rate determination so that the oxygen partial pressure in the vicinity of the diffusing resistor-side electrode 34 is reduced to almost zero and an electromotive force depending on the reference electrode-side oxygen partial pressure is generated. This electromotive force is the same with an electromotive force E known by the expression of Manerunst and it is given by the following equation.

$$E = \frac{RT}{4F} \cdot \ln \frac{Pd}{Pa} \quad (1)$$

Here, Pd is the oxygen partial pressure in the diffusing layer, Pa the oxygen partial pressure in the atmosphere, R the gas constant, T the temperature, and F the Faraday constant.

In other words, the interelectrode voltage Vs is the sum of the voltage drop due to the oxygen pump current and the electromotive force E and therefore it is given by the following equation $$V_s = R_i I_p + \frac{RT}{4F} \ln \frac{Pd}{Pa} \quad (2)$$

Figure 7:
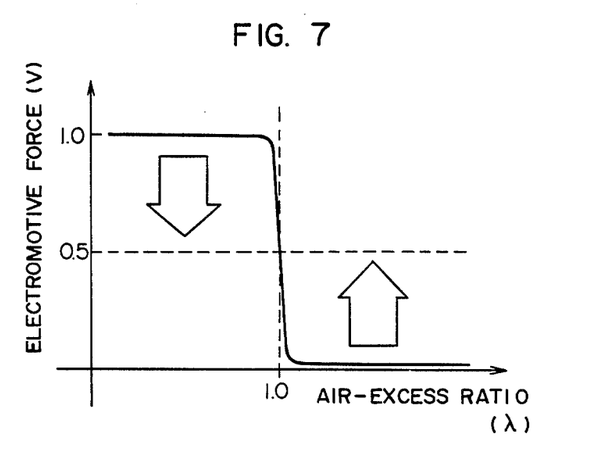
FIG. 7 is an electromotive force characteristic diagram of the air-fuel ratio sensor.

As shown in FIG. 7, the electromotive force varies abruptly at around a theoretical air-fuel ratio point ($\lambda=1$) so that it is about 1 V when the air-fuel ratio is rich and about 0 V when lean.

Figure 8:
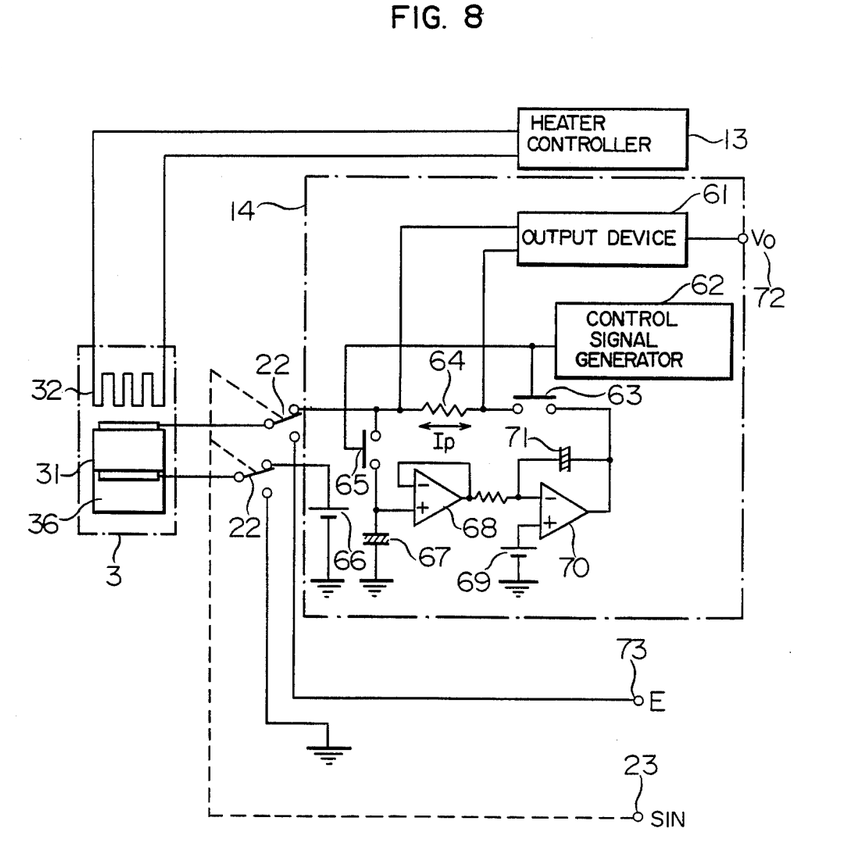
FIG. 8 is a circuit diagram showing the drive circuit.

In the FIG. 8, the change-over between switches 22, 22 is effected by the signal Sin from a terminal 23 of the I/O port 16. When the switches 22 are in the positions shown, the air-fuel ratio 3 is connected to the drive circuit 14 and the air-fuel ratio of the present invention is detected. When the movable contacts of the switches 22 are moved to the lower positions, the restoration time for determining a correction factor due to the aging of the diffusing resistor is measured.

A control signal generator 62 alternately turns on and off switches 63 and 65 at intervals of the order of several msec. During the ON period of the switch 65, a voltage obtained by superposing the voltage of a dc power source 66 or the interelectrode voltage of the air-fuel ratio sensor 3, is sampled and held in a capacitor 67. One electric terminal of the power supply of the engine control apparatus is usually connected to the ground potential and therefore the measurement by the air-fuel ratio sensor can be achieved only on one side of rich and lean sides, since the sensor output becomes negative potential on another side of rich and lean sides. In order to achieve the measurement on both sides of rich and lean sides, a voltage of a DC power source 66 is applied to one electrode of the sensor 3 to shift a voltage level of the one electrode by the voltage of the power source 66 from the ground potential. As a result, a voltage obtained by superposing the voltage of the power source 66 on the interelectrode voltage of the sensor 3 is charged and held by the capacitor 67. This sample-hold voltage is amplified by an operation amplifier 68 (the input impedance of the amplifier 68 is substantially infinite and the amplification degree thereof is substantially one.) and then applied to the negative terminal of a differential amplifier 70, thereby comparing the voltage with the desired voltage of a voltage source 69 which is to be controlled.

Figure 9:
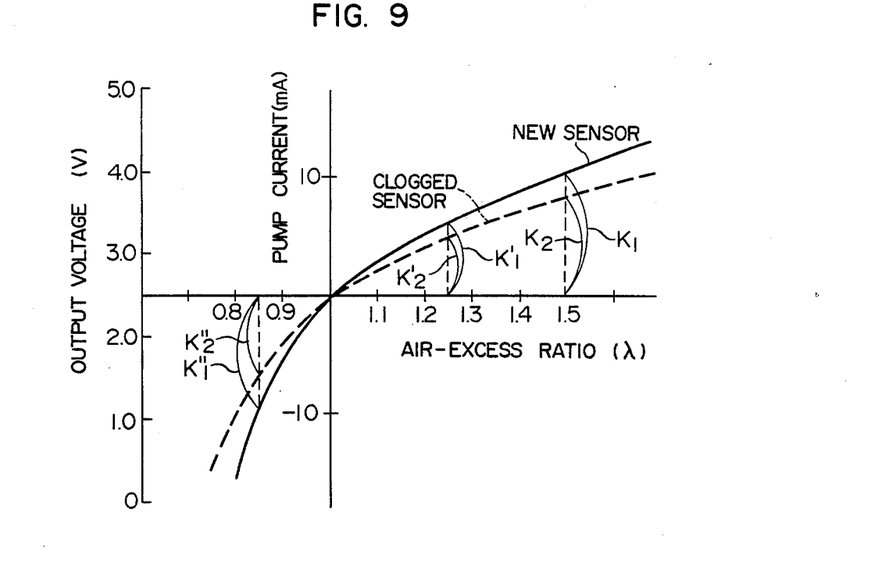
FIG. 9 is an air-fuel ratio characteristic diagram of the air-fuel ratio sensor.

An output of the differential amplifier 70 having a capacitor 71 is substantially equal to the voltage which superposes the voltage of the power source 66 on the interelectrode voltage $V_{sl}$ shown in FIG. 6. Next, when the switch 65 was turned off and the switch 63 was turned on, the voltage which superposes the voltage of the power source 66 on the voltage $V_{sl}$ shown in FIG. 6 is applied to the sensor 3 so that the interelectrode voltage is substantially equal to the voltage $V_{sl}$. Accordingly, the pump current $I_p$ is determined by the air-fuel ratio of gas to be measured. The current $I_p$ is changed to a voltage value by a resistor 64 and then be applied to an A-D converter through an output device 61 and be converted into a digital value. The relation between the current $I_p$ and the air-fuel ratio is shown in FIG. 9. The relation curve data shown by solid line in FIG. 9 is stored in a memory ROM 18 in FIG. 3. An actual air-fuel ratio is calculated on the basis of the pump current $I_p$ and the relation curve data. A target value of the air-fuel ratio is set to the optimum value which corresponds to an actual engine operation state. The fuel injection amount into the engine is so controlled that the air-fuel ratio calculated on the basis of the current $I_p$ coincides with the set optimum air-fuel ratio.

It is desirable that the voltage $V_{sl}$ shown in FIG. 6 is changed along the middle broken line and the voltage to be held in the capacitor 67 should be renewed in accordance with the change of the air-fuel ration. In order to renew to voltage of the capacitor 67, the switches 63 and 65 are alternatively turned on or off to hold the voltage $V_{sl}$ and repeat the measurement of the pump current $I_p$ Semiconductor switches are used as switches 63 and 65.

The above is described as to where the relation between the pump current $I_p$ and the air-fuel ratio is constant, but the relation is changed in actual. The present invention relates to calibration of such a relation as mentioned hereinafter.

Where the diffusing resistor layer 36 of the air-fuel ratio sensor 3 is fouled or clogged by impurities such as carbon caused during the exhaust period or a crack is caused in the diffusing resistor layer 36 by thermal shock or the like, the diffusion constant of the diffusing resistor layer 36 is varied. When this occurs, it is no longer possible to detect the accurate air-fuel ratio corresponding to the oxygen pump current value thus failing to perform the proper air-fuel ratio control.

FIG. 9 shows the output (oxygen pump current) or air-excess ratio characteristics of new and clogged air-fuel ratio sensors. The difference in characteristic is due to the difference in diffusion constant between the two sensors. Even if the difference in characteristic causes the difference in air-excess ratio characteristic, the changing rates K of the air-excess ratios for the respective air-fuel ratios are the same. More specifically, in FIG. 9, when the air-excess ratios are 1.5, 1.25 and 0.85, respectively, the ratio between the respective pump currents $K_1$ and $K_2$, $K_1'$ and $K_2'$, and $K_1''$ and $K_2''$ of the two characteristics is equal to the constant value K $$K = \frac{K_2}{K_1} = \frac{K_2'}{K_1'} = \frac{K_2''}{K_1''} \tag{3}$$

Thus, this means that the rate of change K of the air excess ratio is proportional to the rate of change D of the diffusion constant and it is given by the following equation $$K = aD \tag{4}$$

where a is a constant.

Figure 10:
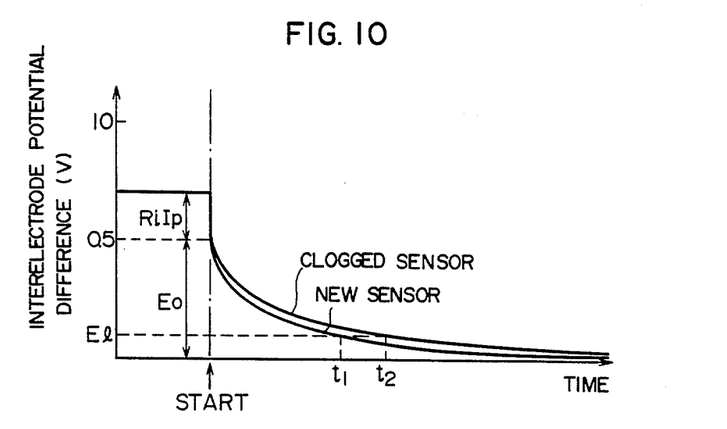
FIG. 10 is an electromotive force restoration characteristic diagram of the air-fuel ratio sensor.

FIG. 10 shows the method of obtaining the diffusion constant of the diffusing resistor layer 36 from the electromotive force restoration time. In the case of FIG. 10, the air-fuel ratio of the exhaust gas is lean. The voltage given by equation (2) is applied as the potential difference $V_s$ between the electrodes 34 and 35 of the sensor cell. Assuming now that the oxygen pump current is stopped, the interelectrode potential difference includes only the controlled electromotive force $E_0$ which is under control. However, the stopping of the oxygen pump current $I_p$ causes natural diffusion of the various gases in the exhaust. As a result, the air-fuel ratio in the diffusion resistor layer gradually reaches the air-fuel ratio of the exhaust gas. Since the air-fuel ratio of the exhaust gas is lean at this time, the electromotive force E decrease toward the restored voltage of 0 V. When the air-fuel ratio is rich, the electromotive force E is restored to 1 V. The rate of change T in restoration time between the new and clogged sensors is given by the following equation on the basis of times $t_1$ and $t_2$ each indicating the time interval between the stopping of the oxygen pump current and the time that the interelectrode potential difference reaches a given restored voltage $E_l$ $$T = t_2/t_1 \tag{5}$$

where $t_1$=restoration time of the new sensor, and $t_2$=restoration time of the clogged sensor.

From this it will be seen that the changing rate D of the diffusion constant is proportional to the changing rate T of the restoration time $$D = bT \tag{6}$$

where b is a constant.

Therefore, the changing rate K of the output can be given from the restoration time of the electromotive force by the following equation (7)

$$K = abT = ab\frac{t_2}{t_1} = \alpha\frac{t_2}{t_1} \tag{7}$$

where $\alpha = ab$ is a constant.

The procedure will now be described with reference to the flow chart of FIG. 1. Firstly, if the air-fuel ratio changes from rich to lean or lean to rich during the measurement of a restoration time, the restored electromotive force is varied failing to measure the accurate restoration time. Therefore, it is desirable that the air-fuel ratio of the exhaust gas is maintained constant. For this reason, while the measurement may be made in any operating condition where the air-fuel ratio is stable, the air-fuel ratio is more stable after the engine has been stopped and thus the restoration time is measured during this period of time. Therefore, at a step 40, it is determined that the ignition switch 12 has been turned off, and the stopping of the engine is confirmed at a step 41. At a step 42, it is determined whether the air-fuel ratio of the exhaust gas is lean or rich. This determination can be made in dependence on the direction of flow of the oxygen pump current. In other words, as will be seen from FIG. 5, when the air-fuel ratio is lean, the oxygen partial pressure in the exhaust gas is high so that the oxygen pump current becomes positive, whereas when the air-fuel ratio is rich, the oxygen pump current becomes negative. Also, since the oxygen pump current is reduced to zero when there is no diffusion of oxygen in the diffusing resistor layer and hence the oxygen partial pressure is stable, the determination can be made depending on whether the detection output $V_0$ is higher or lower than that obtained in such a case. At steps 43 and 44, the restored electromotive force $E_l$ and new sensor restoration time $t_1$, corresponding to the air-fuel ratio of the exhaust gas, are read from the memory in accordance with the lean-state controlled voltage VL or the richstate controlled voltage VR. It is to be noted that the restoration time $t_1$ of the new sensor is measured in the brand-new condition by the same method as the steps 40 to 50 and the result is stored in the ROM 18 at a step 57. Moreover, data of a standard sensor may be stored in the ROM 18 as a program. Since, upon restoration, the electromotive force $E_0$ changes logarithmically with time, if the electromotive force $E_l$ is set to the limit value, that is, to 0 V when the air-fuel ratio is lean and to 1 V when rich, this is not desirable since the restoration time becomes not only excessively long but also inaccurate. Thus, the restored electromotive force $E_l$ should preferably be set with respect to the controlled electromotive force $E_0$ such that $E_0 > E_l > 0$ when the air-fuel ratio is lean and $E_0 < E_l < 1$ (V) when rich.

Also, if the new-sensor restoration time $t_1$ is set to be the same for both the lean and rich air-fuel ratios, only the single memory will be suffice for the restoration time $t_1$. At a step 45, the change-over between the switches 22 of FIG. 8 is effected and the supply of the oxygen pump current is stopped. Simultaneously, the sensor 3 is connected to the electromotive force measuring circuit. However, if the electromotive force has been measured since the supply of the oxygen pump current, there is no need to effect the change-over. At a step 46, the timer is started. At steps 47 and 48, the electromotive force $E_0$ is measured until it becomes equal to the restored electromotive force $E_l$ and upon the restoration a transfer is made to a step 49 where the timer is stopped. At a step 50, the restoration time $t_2$ is determined. At a step 51, in accordance with the restoration time $t_2$ and the new sensor restoration time $t_1$ a rate of change $K_2$ of the output is determined for use as a correction factor. At a step 52, the processing is ended if the correction factor $K_2$ is equal to the preceding correction factor $K_1$ If it is not, the memory is rewritten at steps 53 and 54 thereby completing the processing. When this occurs, a return is made from the calibration subroutine to the main routine of the air-fuel ratio sensor 3 and the air-fuel ratio control of the engine is performed.

In accordance with this embodiment, there is an effect that any aging of the air-fuel ratio sensor is calibrated thus always controlling the engine at the proper air-fuel ratio.

By computing a correction factor in the above-mentioned manner, the characteristic of a new sensor can be determined by computation in accordance with the characteristic of the clogged sensor shown in FIG. 9.

Figure 1:
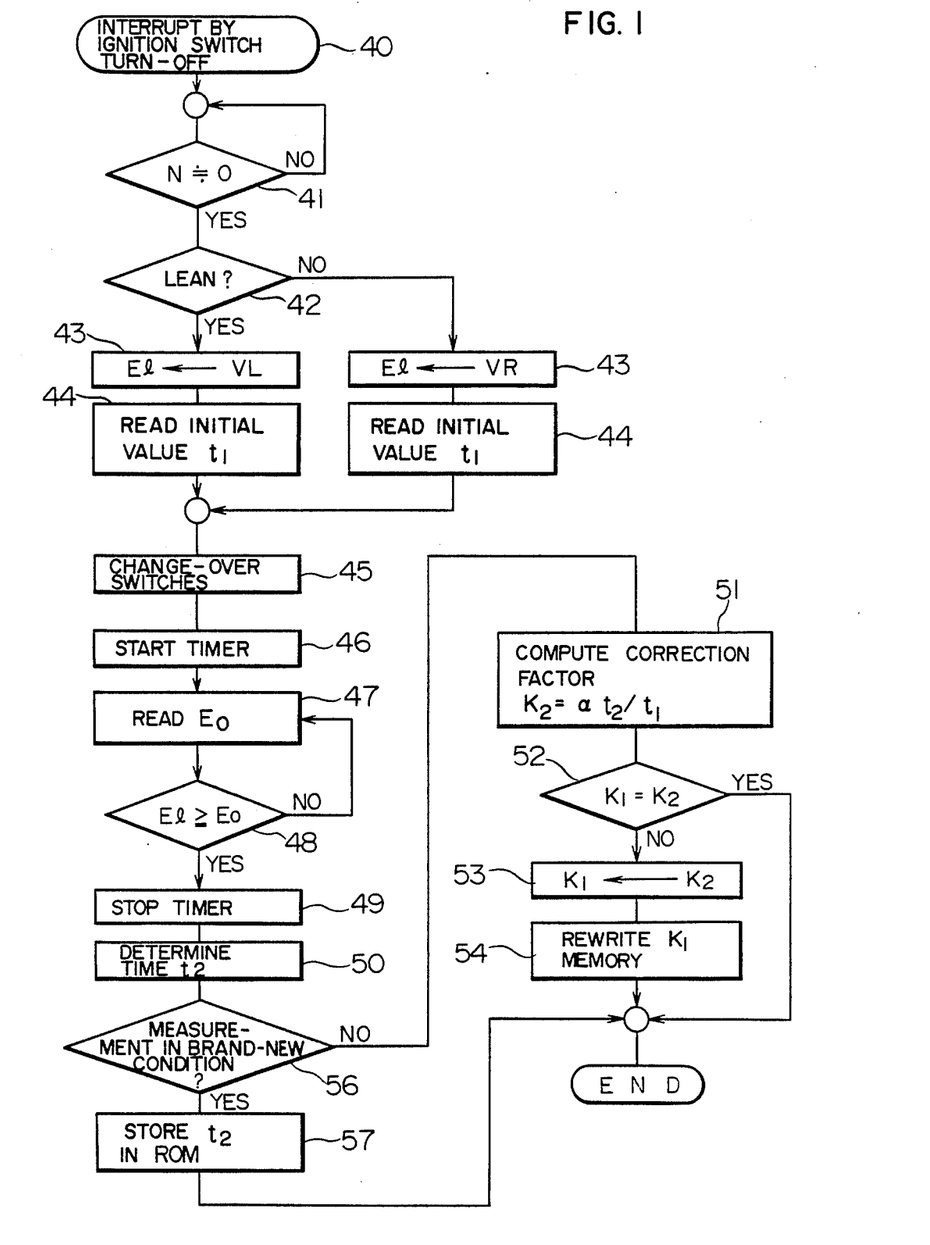
FIG. 1 is a sensor calibration flow chart showing the operation of an embodiment of the present invention.
Figure 11:
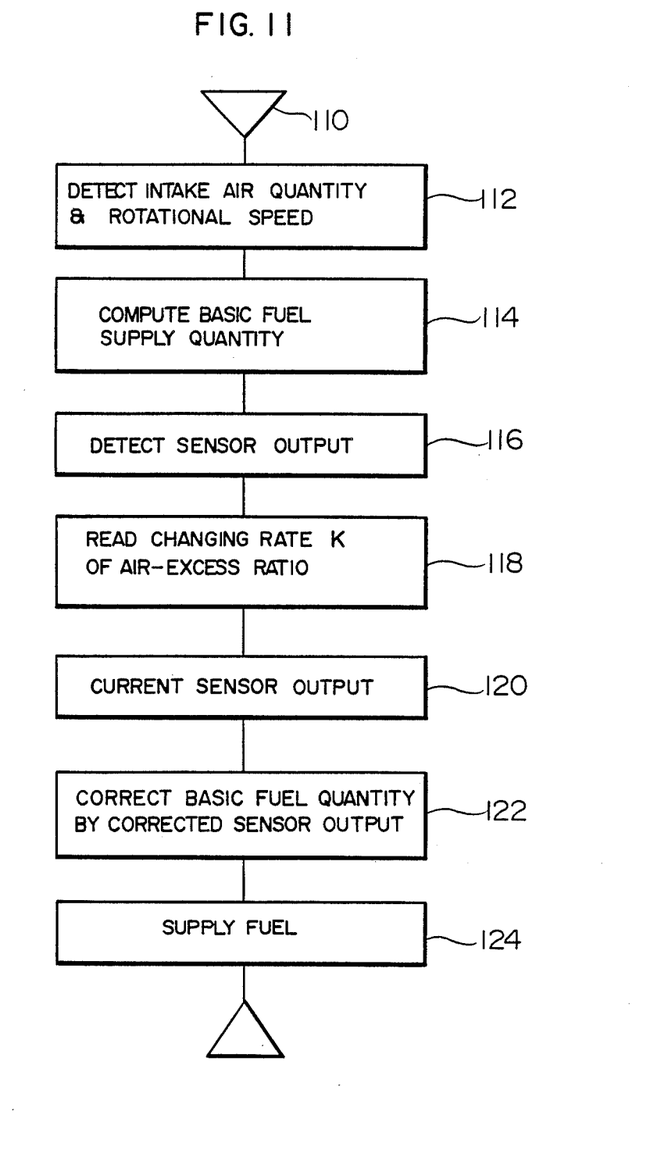
FIG. 11 is an engine fuel control flow chart.

FIG. 11 is an engine control flow diagram in which the changing rate D of the diffusion coefficient detected by the flow of FIG. 1 is used to correct the output of the air-fuel ratio sensor and the corrected output is used to correct the quantity of fuel supplied. A program 110 is executed at intervals of a given period. At a step 112, the required information for operating the engine, such as, an intake air flow Q and an engine rotational speed N are measured. At a step 114, a basic fuel supply quantity is computed from the measured values in accordance with a known method. At a step 116, the output of the air-fuel ratio is detected. At a step 118, the changing rate D of the diffusing resistor detected by the flow of FIG. 1 is read from the memory so that the detected value of the air-fuel ratio sensor is corrected in accordance with equation (3) at a step 120. In other words, the detected value of the air-fuel ratio sensor is corrected by multiplying it by the changing rate K. At a step 122, in accordance with the corrected air-fuel ratio the basic fuel supply quantity is corrected by the known method and the corrected value is set in the counter 17 of FIG. 3 at a step 124 thereby supplying the fuel.

In accordance with the present invention, there is an effect that even if the air-fuel ratio sensor is aged, the desired calibration can be effected without using any reference gas and the engine can always be controlled at the proper air-fuel ratio.

We claim:

1. An air-fuel ratio control apparatus for an internal combustion engine comprising:

a solid electrolyte having a first electrode arranged on one surface thereof to contact with the atmosphere and a second electrode arranged on the other surface thereof to contact with an exhaust gas from said engine through a diffusing resistor;

means for applying a voltage across said first and second electrodes to detect an oxygen pump current flowing through said solid electrolyte;

means for computing a correction factor relating to a change in a diffusion coefficient of said diffusing resistor; and means for determining an air-fuel ratio of said exhaust gas in accordance with said correction factor and the oxygen pump current detected by said detecting means.

2. An apparatus according to claim 1, wherein said correction factor computing means comprises means for determining said correction factor in accordance with a restoration time required for an electromotive force across said first and second electrodes after the stopping of said oxygen pump current to be restored to a given value.

3. An apparatus according to claim 1, wherein said correction factor computing means comprises:

first detecting means for detecting a restoration time required for an electromotive force across said first and second electrodes after the stopping of said oxygen pump current to be restored to a given value when said solid electrolyte is brand-new;

a memory for storing the restoration time detected by said first detecting means;

second detecting means for detecting a restoration time required for an electromotive force across said first and second electrodes after the stopping of said oxygen pump current to be restored to a given value during the computation of a correction factor; and means for determining said correction factor in accordance with the ratio of the restoration time obtained by said second detecting means to the restoration time obtained by said first detecting means.

4. An apparatus according to claim 3, wherein said correction factor computing means further comprises means for writing the correction factor obtained by said determining means into another memory.

5. An apparatus according to claim 4, wherein said correction factor computing means further comprises means for rewriting the correction factor previously obtained by said determining means and stored in said another memory.

6. An apparatus according to claim 1, wherein said determining means comprises means for correcting the oxygen pump current detected by said detecting means in accordance with said correction factor, and means for determining an air-fuel ratio of said exhaust gas in accordance with the oxygen pump current corrected by said correcting means.

7. An air-fuel ratio control apparatus for an internal combustion engine comprising:

a sensor for detecting an air-fuel ratio of an exhaust gas from said engine, said sensor including a solid electrolyte having a first electrode arranged on one surface thereof to contact with the atmosphere and a second electrode arranged on the other surface thereof to contact with an exhaust gas from said engine through a diffusing resistor;

means for computing a correction factor for correcting the air-fuel ratio detected by said sensor in accordance with a variation with time of a diffusion coefficient of said diffusing resistor of said sensor;

means for correcting the air-fuel ratio from said sensor in accordance with the correction factor computed by said computing means; and means for controlling the quantity of fuel supplied to said engine in accordance with the air-fuel ratio corrected by said correcting means.

8. An air-fuel ratio control apparatus for an internal combustion engine comprising:

a sensor for detecting an air-fuel ratio of an exhaust gas from said engine, said sensor including a solid electrolyte having a first electrode arranged on one surface thereof to contact with the atmosphere and a second electrode arranged on the other surface thereof to contact with the exhaust gas from said engine through a diffusing resistor;

means for detecting a diffusion time of said exhaust gas in said diffusing resistor of said sensor;

means for computing a correction factor in accordance with said diffusion time; and means for controlling the quantity of fuel supplied to said engine in accordance with the correction factor computed by said computing means.

* * * * *